United States Patent
Hosoya et al.

(10) Patent No.: US 10,918,260 B2
(45) Date of Patent: Feb. 16, 2021

(54) ENDOSCOPIC IMAGE OBSERVATION SUPPORT SYSTEM

(71) Applicant: OLYMPUS CORPORATION, Tokyo (JP)

(72) Inventors: Ryoichi Hosoya, Tokyo (JP); Takashi Nagata, Tokyo (JP); Isao Tateshita, Tokyo (JP); Ryo Inomata, Tokyo (JP); Ryo Oguma, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/453,171

(22) Filed: Jun. 26, 2019

(65) Prior Publication Data

US 2019/0313883 A1 Oct. 17, 2019

Related U.S. Application Data

(63) Continuation of application No. PCT/JP2017/034533, filed on Sep. 25, 2017.

(30) Foreign Application Priority Data

Feb. 2, 2017 (JP) .............................. JP2017-017914

(51) Int. Cl.
*A61B 1/00* (2006.01)
*A61B 1/045* (2006.01)
(Continued)

(52) U.S. Cl.
CPC ...... *A61B 1/00009* (2013.01); *A61B 1/00045* (2013.01); *A61B 1/045* (2013.01);
(Continued)

(58) Field of Classification Search
CPC ... A61B 1/00; A61B 1/00009; A61B 1/00045; A61B 1/045; G02B 23/24; G06Q 50/22;
(Continued)

(56) References Cited

U.S. PATENT DOCUMENTS 5,740,801 A * 4/1998 Branson ................ G06F 19/321
128/920
2003/0023150 A1* 1/2003 Yokoi ................ A61B 1/00032
600/300
(Continued)

FOREIGN PATENT DOCUMENTS

JP 2003-038425 A 2/2003
JP 2004-005364 A 1/2004
(Continued)

OTHER PUBLICATIONS

International Search Report dated Dec. 12, 2017 issued in International Application No. PCT/JP2017/034533.
(Continued)

*Primary Examiner* — James T Boylan
(74) *Attorney, Agent, or Firm* — Scully, Scott, Murphy & Presser, P.C.

(57) ABSTRACT

For each finding, a finding image recorder records as a finding image an endoscopic image captured in the past. A compression processing unit performs a compression process on an endoscopic image captured by a capsule endoscope so as to generate a compressed image. A similarity determination unit determines, when the compression processing unit performs a compression process on the endoscopic image, whether or not the endoscopic image is similar to a finding image recorded in the finding image recorder. When the endoscopic image is determined to be similar to the finding image by the similarity determination unit, the compression processing unit adds predetermined information to the compressed image.

8 Claims, 4 Drawing Sheets

(51) Int. Cl.
  *G02B 23/24* (2006.01)
  *G16H 30/40* (2018.01)
(52) U.S. Cl.
  CPC .... *G02B 23/24* (2013.01); *G06T 2207/10068* (2013.01); *G16H 30/40* (2018.01)
(58) Field of Classification Search
  CPC .......... G06T 2207/10068; G16H 10/60; G16H 30/20; G16H 30/40
  See application file for complete search history.

(56) References Cited

U.S. PATENT DOCUMENTS

| | | | | |
|---|---|---|---|---|
| 2007/0066875 | A1* | 3/2007 | Horn | A61B 1/041 600/300 |
| 2007/0216781 | A1* | 9/2007 | Miyanohara | H04N 5/76 348/231.99 |
| 2012/0316421 | A1* | 12/2012 | Kumar | A61B 1/041 600/407 |
| 2015/0248589 | A1* | 9/2015 | Broache | G06K 9/6807 382/182 |

FOREIGN PATENT DOCUMENTS

| | | |
|---|---|---|
| JP | 2007-075163 A | 3/2007 |
| JP | 2007-105458 A | 4/2007 |
| JP | 2007-228337 A | 9/2007 |
| JP | 2009-189475 A1 | 8/2009 |
| WO | 2017/006618 A1 | 1/2017 |

OTHER PUBLICATIONS

International Preliminary Report on Patentability together with the Written Opinion from related International Application No. PCT/JP2017/034533 dated Aug. 6, 2019.

* cited by examiner

ENDOSCOPIC IMAGE OBSERVATION SUPPORT SYSTEM

CROSS-REFERENCE TO RELATED APPLICATIONS

This application is based upon and claims the benefit of priority from the prior Japanese Patent Applications No. 2017-017914, filed on Feb. 2, 2017, and International Application No. PCT/JP2017/034533, filed on Sep. 25, 2017, the entire contents of which are incorporated herein by reference.

BACKGROUND OF THE INVENTION

1. Field of the Invention

The present invention relates to a system for supporting the observation of endoscopic images captured by a capsule endoscope.

2. Description of the Related Art

Japanese Patent Application Publication No. 2004-5364 discloses a similar image retrieval system that retrieves, from among a large number of pieces of subject image data stored in an image database, similar image data having a portion whose image characteristics are similar to those of retrieval image data of a subject image to be retrieved and outputs retrieval result information.

In a capsule endoscopic examination, tens of thousands of images are captured. The image interpreter observes continuously played back endoscopic images and extracts images that contain abnormal findings. However, since the number of images is enormous, the burden of image interpretation is significant. Therefore, the development of a technology is desired that allows image observation by the image interpreter to be efficiently performed.

SUMMARY OF THE INVENTION

In this background, a purpose of the present invention is to provide a technology that allows image observation by the image interpreter to be efficiently performed.

One embodiment of the present invention relates to an endoscopic image observation support system for supporting observation of an endoscopic image captured by a capsule endoscope and for generating a plurality of compressed images by performing a compression process on a plurality of endoscopic images captured by the capsule endoscope. This system includes: a processor including hardware; and a finding image recorder that records as a finding image an endoscopic image captured in the past, wherein the processor is configured to: determine, when performing a compression process on an endoscopic image, whether or not the endoscopic image is similar to a finding image recorded in the finding image recorder; add, when the endoscopic image is determined to be similar to the finding image, predetermined information to a compressed image of the endoscopic image; and record the compressed image in an endoscopic image recorder.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Figure 1:
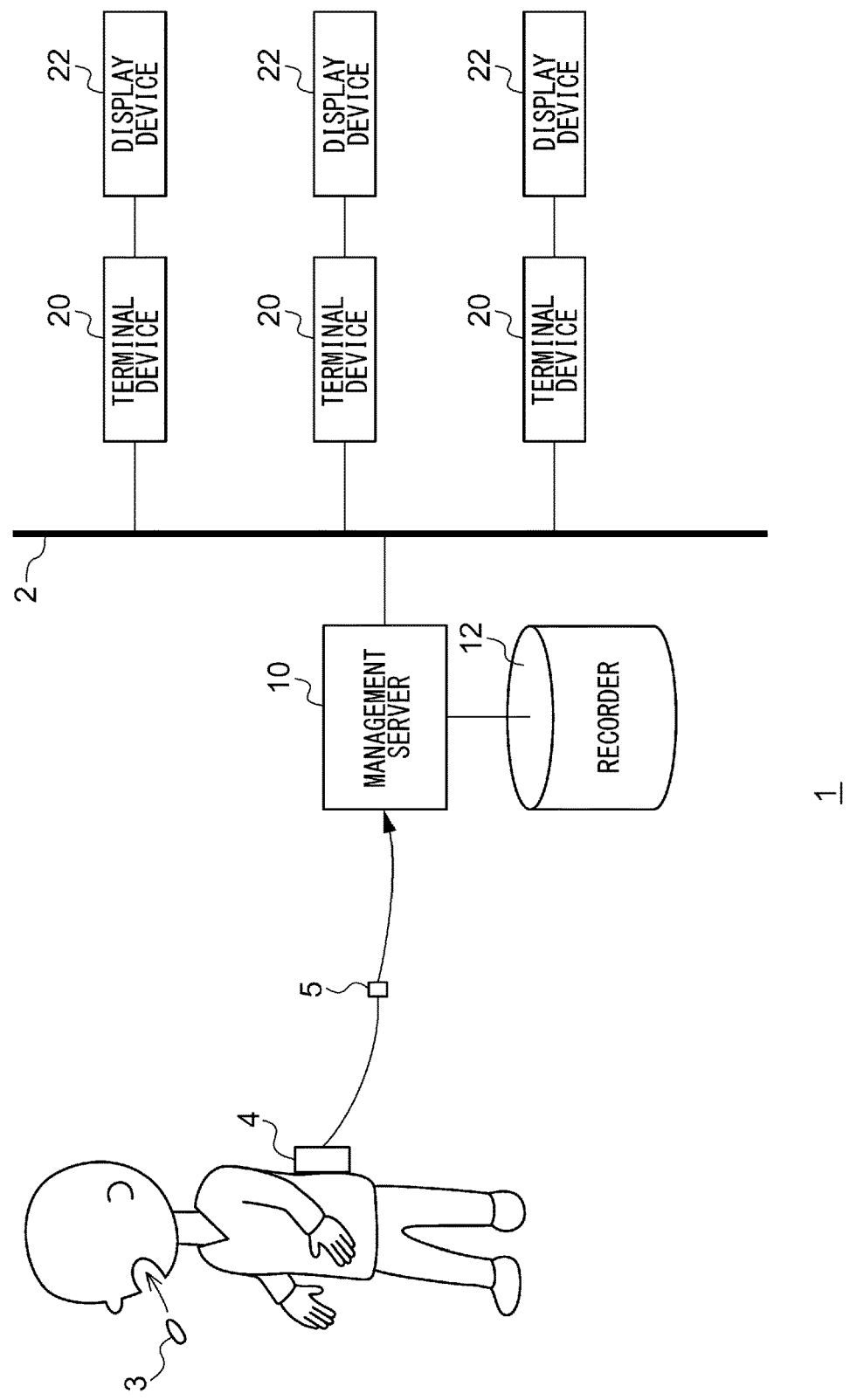
FIG. 1 is a diagram for explaining the outline of an image observation support system of a capsule endoscope according to an embodiment.

FIG. 1 is a diagram for explaining the outline of an image observation support system of a capsule endoscope according to an embodiment. An endoscopic image observation support system 1 supports observation of a capsule endoscopic image by an image interpreter. In an examination where a usual endoscope is used, a doctor observes an image captured by an endoscope inserted in a patient's body in real time on a display and makes a diagnosis. However, a capsule endoscopic examination is different from a usual endoscopic examination in that the image interpreter collectively observes a large amount of images captured in the past by a capsule endoscope.

In a capsule endoscopic examination, the patient swallows a capsule endoscope 3 having a built-in ultracompact camera from the mouth, with an antenna (not shown) being attached to the abdomen and a receiver 4 being attached to the waist by a belt. The capsule endoscope 3 captures still images periodically as it moves through the digestive tract and transmits captured images to the receiver 4 through the antenna. A detachable recording medium 5 is mounted in the receiver 4, and the receiver 4 records a captured image that has been received in the recording medium 5. In the case where the capsule endoscope 3 images the inside of the body, for example, every 0.5 seconds, about 60,000 endoscopic images are recorded in the recording medium 5 when the imaging of the inside of the body is completed in about 8 hours.

When the antenna and the receiver 4 are collected from the patient, the recording medium 5 is removed from the receiver 4 and mounted in a data reader connected to a management server 10. The data reader reads about 60,000 endoscopic images recorded in the recording medium 5 and transmits the endoscopic images to the management server 10. The data reader may be an external device that becomes connected to the management server 10 by a USB cable or the like. The recording medium 5 may be inserted in a data reading slot provided in the management server 10 such that the endoscopic images are read out. The recording medium 5 may be a memory built in the receiver 4, and, in this case, the data reader may read endoscopic images recorded in the recording medium 5 from a data terminal of the receiver 4.

The management server 10 performs a predetermined image process on endoscopic images read from the recording medium 5 and records the images in a recording device 12. The recording device 12 may be comprised of a hard disk drive (HDD) or a flash memory. Since the endoscopic images recorded in the recording medium 5 are uncompressed RAW (raw) images or RAW images on which only lossless compression has been performed, the data size thereof is very large. Therefore, the management server 10 performs a predetermined lossy compression process on the endoscopic images (hereinafter, sometimes referred to as "endoscopic RAW images") that are RAW images so as to reduce the data size thereof and records the images in the recording device 12.

The management server 10 may have a function of managing order information for an endoscopic examination, image interpretation report information, and the like in addition to a function of performing a predetermined image process on endoscopic RAW images. In the embodiment, the management server 10 is in charge of the image process on endoscopic RAW images. However, another device, for example, a terminal device 20 may perform the image process on the endoscopic RAW images and records the images in the recording device 12.

As will be described later, the management server 10 according to the embodiment has a function of determining whether or not an endoscopic RAW image is similar to an endoscopic image for which an abnormal finding has been confirmed in the past when performing a compression process on the endoscopic RAW image and adding predetermined information to the image that has been compressed when the endoscopic RAW image is determined to be similar.

A plurality of terminal devices 20 are connected to the management server 10 via a network 2 such as a local area network (LAN). For example, the terminal devices 20 are personal computers assigned to doctors or technicians or the like and are connected to display devices 22 to enable output to be displayed on the screen. The terminal devices 20 may be laptop computers integrated with the display devices or portable tablets.

A terminal device 20 is able to access the management server 10 and display the endoscopic images recorded in the recording device 12 on the display device 22. It is preferable that the management server 10 runs a playback application for endoscopic images, sequentially plays back several tens of thousands of endoscopic images efficiently, and provides the endoscopic images to the terminal device 20. The playback application executes a playback process of the endoscopic images in accordance with a playback mode and playback speed that are selected by the terminal device 20.

One of the purposes of a capsule endoscopic examination is to find blood points in a digestive tract. Upon acquiring the endoscopic RAW images from the recording medium 5, the management server 10 executes an analysis application so as to perform the image process, thereby identifying an endoscope RAW image determined to have captured a bleeding state. The management server 10 adds flag information showing that there exists a bleeding state when compressing the endoscopic RAW image that has been identified. For example, when the redness in an endoscopic image exceeds a predetermined threshold value, the management server 10 determines that the image is an image in which a bleeding state has been captured. The playback application may notify the image interpreter when playing back the image to which the flag information has been added that a bleeding state is highly likely to have been captured in the image such that the image interpreter can easily recognize that the image is a played back image determined to be a strongly reddish image.

The moving speed of the capsule endoscope 3 in a digestive tract varies depending on the location. Where the moving speed is low, the variation between endoscopic images captured is small. In this background, the analysis application compares endoscopic RAW images captured successively in time and performs the grouping of a group of endoscopic images with small change. The playback application has a playback mode for shortening the playback time of grouped endoscopic images. When this playback mode is selected by the image interpreter, the shortening of the observation time can be realized. For the playback application, a plurality of types of playback modes for the time-shortening may be prepared. When the playback mode for continuously playing back endoscopic images at a constant speed is referred to as the first mode, the playback application according to the embodiment has, as playback modes for the time-shortening, the second mode where an endoscopic image group that has been grouped is switched and played back at a speed higher than usual and the third mode where one or more images are extracted from the endoscopic image group and played back. The image extracted in the third mode may be an image having high similarity with the previous and/or following images or an image in which the entire subject has been captured. Both the second mode and the third mode contribute to the shortening of the overall observation time as compared to the first mode.

Furthermore, the analysis application according to the embodiment performs a similarity determination process of comparing an endoscopic RAW image with a finding image recorded in the recording device 12 and determining whether or not the endoscopic RAW image is similar to the finding image. A finding image is an image determined to include an abnormal finding through image diagnosis by a doctor in the past and is an image to be compared with a newly captured endoscopic RAW image in the similarity determination process. That is, if the degree of similarity between the newly captured endoscopic RAW image and the finding image is high, it is determined that the endoscopic image is highly likely to include an abnormal finding associated with the past finding image.

Therefore, for each finding, the recording device 12 according to the embodiment records as a finding image an endoscopic image captured in the past. When the doctor prepares an image interpretation report, an endoscopic image including an abnormal finding is associated with information about the finding. From among endoscopic images associated with finding information, the doctor records, as a finding image in the recording device 12 in association with the finding information, an image determined to be appropriate as a comparison image for automatically detecting an abnormal finding through the similarity determination process by the analysis application such as an endoscopic image in which the characteristics of the abnormal finding have been captured clearly.

Typical findings in a capsule endoscopic examination include "ulcer", "erosion", "vascular lesion", etc. In the recording device 12, a plurality of endoscopic images determined to be appropriate as comparison images by the doctor are recorded for each finding. Preferably, the doctor can freely add or delete a finding image to or from the recording device 12. As a result, the doctor deletes a finding image recorded in the recording device 12 if the finding image is not appropriate as a comparison image, and when the doctor finds an endoscopic image considered to be appropriate as a comparison image, the doctor adds the endoscopic image to the recording device 12. By switching finding images in this manner, the similarity determination accuracy can be improved.

The image process by the analysis application described above is performed on all endoscopic RAW images captured in one capsule endoscopic examination when performing the compression process on the endoscopic RAW images. The result of the image process is added as additional information to the endoscopic images that have been compressed. Thereby, when the playback application performs the playback process on the compressed images, the additional information can be reflected in the playback details since the result of the image process is already added to the compressed images.

The terminal device 20 has a function of supporting an image interpretation task by the image interpreter in cooperation with the management server 10. A user interface such as a keyboard, a mouse, etc., is connected to the terminal device 20. The terminal device 20 causes the display device 22 to display a selection screen for an endoscopic image. While looking at the displayed screen, the image interpreter operates the user interface to select an endoscopic image.

Figure 2:
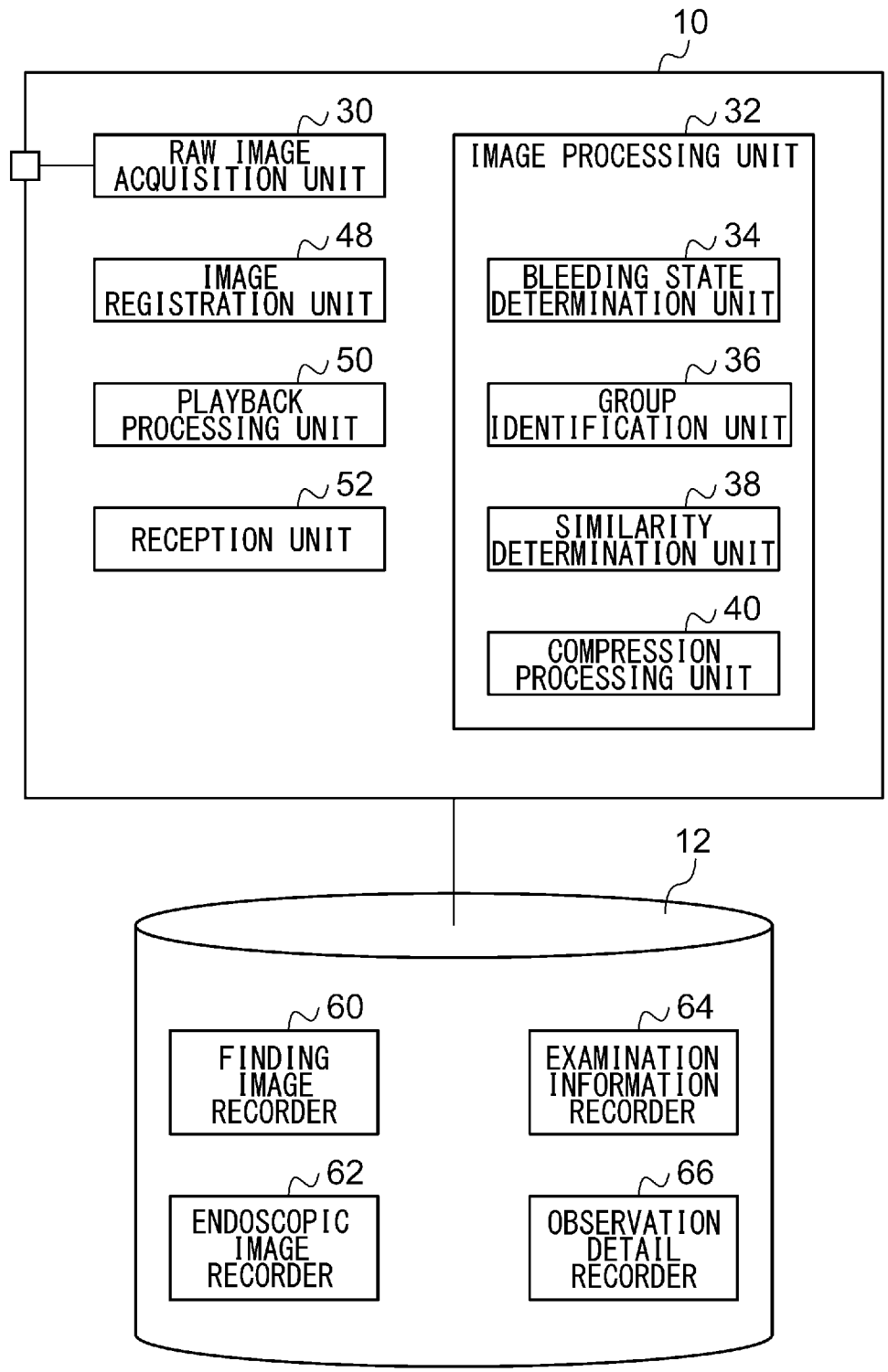
FIG. 2 is a diagram showing the configuration of a management server and a recording device.

FIG. 2 shows the configuration of the management server 10 and the recording device 12. The management server 10 includes a RAW image acquisition unit 30, an image processing unit 32, an image registration unit 48, a playback processing unit 50, and a reception unit 52. The image processing unit 32 has a bleeding state determination unit 34, a group identification unit 36, a similarity determination unit 38, and a compression processing unit 40. Each function of the management server 10 may be realized by executing various applications such as the analysis application, the playback application, etc. The functions of the bleeding state determination unit 34, the group identification unit 36, and the similarity determination unit 38 are realized by the analysis application, and the function of the playback processing unit 50 is realized by the playback application.

The recording device 12 includes a finding image recorder 60, an endoscopic image recorder 62, an examination information recorder 64, and an observation detail recorder 66. For each finding, the finding image recorder 60 records as a finding image an endoscopic image captured in the past. As described above, a finding image is an endoscopic image identified to include an abnormal finding through image diagnosis by a doctor in the past. Based on image registration operation by the doctor, the image registration unit 48 registers an endoscopic image including an abnormal finding in the finding image recorder 60 as a finding image in association with finding information and deletes a finding image from the finding image recorder 60 based on registration cancellation operation by the doctor. For each examination, the endoscopic image recorder 62 records an endoscopic image on which the image process has been performed by the image processing unit 32. The examination information recorder 64 records information on an endoscopic examination, and the observation detail recorder 66 records observation details of an endoscopic image.

The configuration of the management server 10 is implemented by hardware such as a processor, a memory, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both. As described above, the image process on an endoscopic RAW image may be performed by another device other than the management server 10. In that case, the other device has the function of the RAW image acquisition unit 30 and the function of the image processing unit 32.

When the recording medium 5 in which an endoscope RAW image is recorded is mounted to the data reader, the data reader reads the endoscope RAW image from the recording medium 5 and transmits the endoscope RAW image to the management server 10. In the management server 10, the RAW image acquisition unit 30 acquires a plurality of endoscope RAW images that have been transmitted. The RAW image acquisition unit 30 temporarily stores the plurality of endoscope RAW images that have been acquired in the recording device 12, and the image processing unit 32 performs the following image process on all the endoscope RAW images.

Identification of Bleeding Image

The bleeding state determination unit 34 searches for a reddish endoscope RAW image in which a bleeding state is considered to have been captured through image analysis and identifies an image with redness that is stronger than a predetermined threshold value as a bleeding image. The bleeding state determination unit 34 provides information (image ID) for the identification of the bleeding image that has been identified to the compression processing unit 40.

Grouping of Successive Images with Small Variation

The group identification unit 36 extracts a plurality of endoscopic RAW images captured successively and showing small image-to-image variations. The capsule endoscope 3 captures images at a predetermined cycle. Therefore, if the moving speed is low, similar (substantially unvarying) images will be captured successively. The group identification unit 36 extracts a group of endoscopic images with small image-to-image variations and groups the endoscopic images. The group identification unit 36 provides information (group ID) for identifying a group of endoscopic images extracted as a group, the image ID (first image ID) of an image located at the beginning of the group of endoscopic images, and the image ID (last image ID) of an image located at the end of the group of endoscopic images to the compression processing unit 40.

Matching Process with Past Finding Image

The similarity determination unit 38 retrieves a finding image similar to an endoscopic RAW image from among a plurality of finding images recorded in the finding image recorder 60. In other words, the similarity determination unit 38 determines whether or not the endoscopic RAW image is similar to a finding image recorded in the finding image recorder 60. In this similarity determination process, when it is determined that the endoscopic RAW image is similar to the finding image, this endoscopic RAW image is highly likely to show an abnormal finding associated with the finding image determined to be similar.

The finding image recorder 60 may record, as a finding image, a region of interest in a portion of an endoscopic image captured in the past, and the similarity determination unit 38 may then determine whether or not a region similar to the finding image is included in an endoscopic RAW image. In this case, when the doctor registers the finding image in the finding image recorder 60, the doctor marks a part showing an abnormal finding in the endoscopic image as a region of interest, and the similarity determination unit 38 then determines whether or not a region similar to the marked region of interest is included in the endoscopic RAW image. By using the region of interest in which an abnormal finding has been captured instead of the entire endoscopic image as a comparison target for similarity determination, the shortening of the determination time and the improvement of the determination accuracy by the similarity determination unit 38 can be realized. When determining that the endoscopic RAW image is similar to the finding image, the similarity determination unit 38 provides finding information associated with the finding image that has been determined to be similar to the compression processing unit 40 together with the image ID. The similarity determination unit 38 may provide the compression processing unit 40 with the image ID of the finding image that has been determined to be similar.

Compression Process on Endoscope RAW Image

An image process performed by the bleeding state determination unit 34, the group identification unit 36, and the similarity determination unit 38 is performed at the time of a compression process on an endoscopic RAW image performed by the compression processing unit 40. The compression processing unit 40 performs a lossy compression process on an endoscopic RAW image so as to generate a compressed image. The compression processing unit 40 adds elapsed time information from the start of imaging and the image ID to the compressed image. For example, the compression processing unit 40 may compress the endoscopic RAW image in an image format such as JPEG.

At this time, the compression processing unit 40 adds information indicating analysis results provided from the bleeding state determination unit 34, the group identification unit 36, and the similarity determination unit 38 to the compressed image. More specifically, to the compressed image having an image ID provided from the bleeding state determination unit 34, the compression processing unit 40 adds information indicating that the image is a bleeding image. This information may be added as flag information. Further, to respective compressed images having the first image ID and the last image ID provided by the group identification unit 36, the compression processing unit 40 adds information indicating that the images are respectively at the start position and the last position of a group identified by the group ID.

Further, the compression processing unit 40 adds predetermined information to a compressed image having an image ID provided from the similarity determination unit 38. More specifically, to this compressed image, the compression processing unit 40 adds information on a finding associated with a finding image determined to be similar. The compression processing unit 40 may add to the compressed image the image ID of the finding image determined to be similar. The image processing unit 32 operating as described above allows a compressed image to which the result of the image process is added to be generated before the image interpretation performed by the image interpreter. The compression processing unit 40 records the compressed image that has been generated in the endoscopic image recorder 62.

In the above example, the bleeding state determination unit 34, the group identification unit 36, and the similarity determination unit 38 each perform an image process on an endoscopic RAW image before the compression process on the endoscopic RAW image is performed by the compression processing unit 40. In an exemplary variation, the bleeding state determination unit 34, the group identification unit 36, and the similarity determination unit 38 may each perform an image process on a compressed image on which a compression process has been performed. Even in this case, the result of the image process is added to the compressed image by the compression processing unit 40.

A screen that is displayed on the display device 22 at the time of image interpretation by a doctor B will be described in the following. The doctor B enters the user ID to log into a terminal device 20. When the doctor B logs in, the management server 10 supplies examination information stored in the examination information recorder 64 to the terminal device 20, and the display device 22 displays a list of capsule endoscopic examinations. The list of examinations displays examination information such as the patient ID, patient name, examination ID, date and time of examination in a list, and the doctor B selects an examination in which the doctor B is expected to create an image interpretation report. When an examination for a patient ID "A" and an examination ID "0001" is selected from the list of examinations, the playback processing unit 50 generates a selection screen for selecting an endoscopic image and causes the display device 22 to display the selection screen. The terminal device 20 may have the function of the playback processing unit 50.

Figure 3:
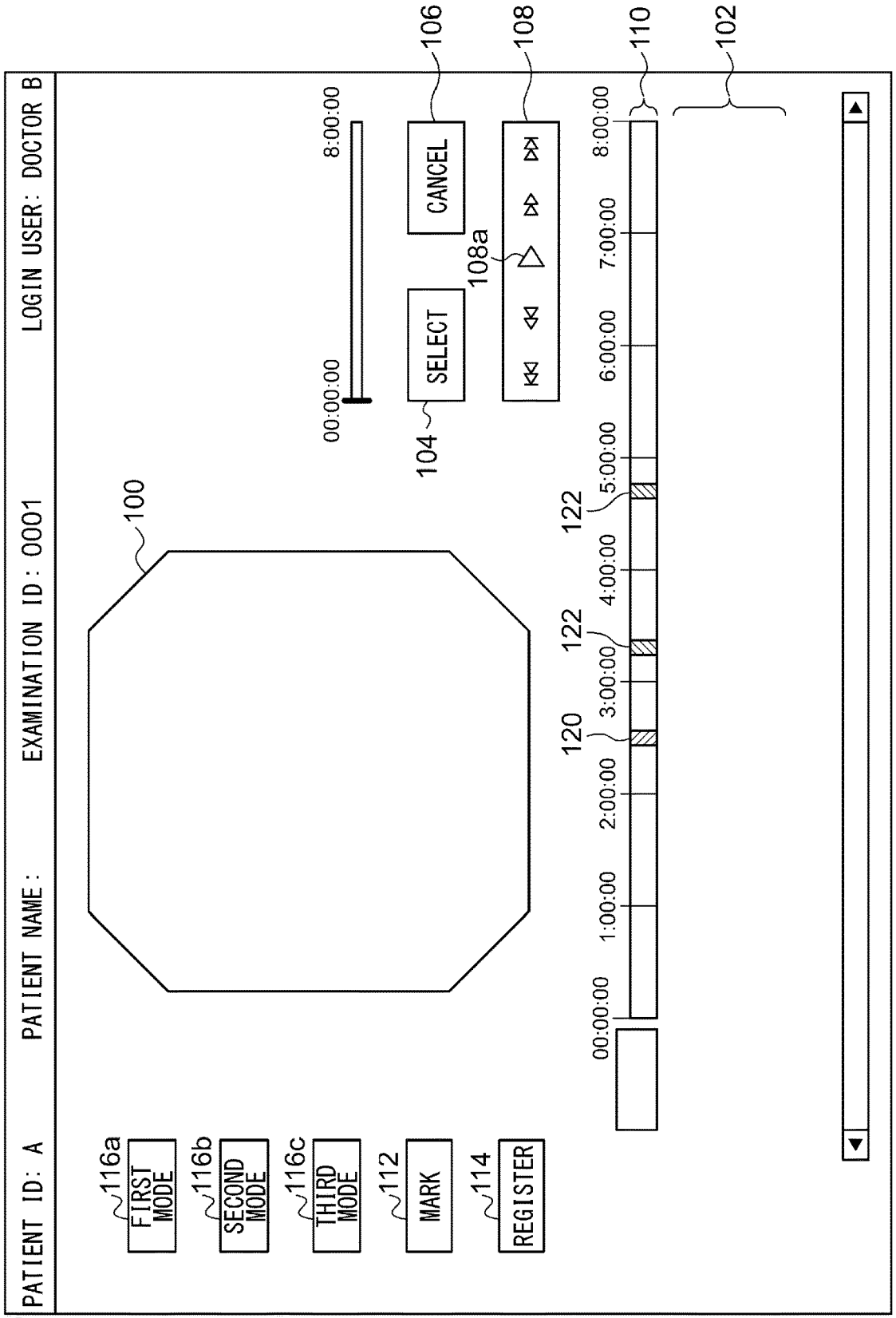
FIG. 3 shows an example of a selection screen for an endoscopic image.

FIG. 3 shows an example of a selection screen for an endoscopic image. The playback processing unit 50 generates a selection screen that includes a playback area 100 for displaying endoscopic images in a switching manner. The playback processing unit 50 displays a compressed image recorded in the endoscopic image recorder 62 on the display device 22. Buttons for controlling the playback operation are displayed in a playback operation area 108 to enable adjustment of the playback speed. When a playback button 108*a* is used, endoscopic images are started to be displayed in a switching manner in the playback area 100. In the playback operation area 108, a pause button is displayed instead of the playback button 108*a*.

When the doctor B uses the pause button while endoscopic images are displayed in the playback area 100 in a switching manner, the switching between endoscopic images is suspended. When the doctor B uses the mouse wheel in this state, the image before or after the paused endoscopic image is displayed in the playback area 100. When the doctor B operates a selection button 104 while the endoscopic image is being paused in the playback area 100, the image is captured and displayed in a selected image display area 102. The selected image displayed in the selected image display area 102 may be selected as an image attached to an image interpretation report later. When the doctor B selects the selected image in the selected image display area 102 and operates a cancel button 106, the selection can be cancelled. For example, the cancel button 106 may be used to keep only a favorably captured image when a plurality of images have been selected for the same finding.

A first mode selection button 116*a*, a second mode selection button 116*b*, and a third mode selection button 116*c* are buttons for setting a playback mode. When the first mode selection button 116*a* is selected, a first mode for playing back an endoscopic image at a constant speed is set as the playback mode. In the initial state of the selection screen, the first mode selection button 116*a* may be in a selected state.

When the second mode selection button 116*b* is selected, a second mode in which a group of endoscopic images that has been grouped is displayed in a switching manner at a speed higher than that for other endoscopic images is set as the playback mode. When the third mode selection button 116c is selected, a third mode in which one or more images are extracted from the group of endoscopic images that has been grouped and are played back is set as the playback mode. Both the second mode and the third mode are prepared in order to streamline the image interpretation by the image interpreter.

A timeline 110 is a user interface for indicating the temporal position of an endoscopic image being played back in the playback area 100 and is also a user interface for displaying an endoscopic image in the playback area 100 in a paused state. The timeline 110 is displayed as a horizontally long rectangular area, and the horizontal axis represents the time from the start to the end of imaging.

When the doctor B places the mouse pointer at a desired part on the timeline 110, the endoscopic image captured at that point of time is displayed in the playback area 100. The doctor B can add a mark for indicating the start position of a site to the timeline 110. When a new site image is played back while viewing endoscopic images played back sequentially in the playback area 100, the doctor B operates a marking button 112 to mark the start position of the site on the timeline. By performing this marking process, the start position of a site can be easily known when reviewing endoscopic images.

On the timeline 110, the playback processing unit 50 displays notification information that is based on information added to a compressed image recorded in the endoscopic image recorder 62. In FIG. 3, the playback processing unit 50 displays one piece of notification information 120 and two pieces of notification information 122 in a display format indicating time ranges in the timeline 110. The notification information 120 and the notification information 122 are information on findings in images included in the time ranges. The playback processing unit 50 changes the display mode of the notification information for each finding and notifies information on the finding according to the difference in the display mode.

For example, the notification information 120 is information on the finding on a pathological abnormality A and specifically is information indicating that the image of the pathological abnormality A is likely to be included. On the other hand, the notification information 122 is information on the finding on a pathological abnormality B and specifically is information indicating that the image of the pathological abnormality B is likely to be included. The playback processing unit 50 refers to additional information of all the images captured in one capsule endoscopic examination so as to obtain the position on the timeline 110 based on the elapsed time information of a compressed image to which information on a finding is added and displays the notification information 120 and the notification information 122.

The playback processing unit 50 displays, for example, the notification information 120 and the notification information 122 in different colors. For example, the playback processing unit 50 displays the notification information 120 in red and the notification information 122 in blue. This allows the image interpreter to understand at a glance that the notification information 120 displayed in red relates to the pathological abnormality A and the notification information 122 displayed in blue relates to the pathological abnormality B. The text "pathological abnormality A" may be displayed in association with the notification information 120, and the text "pathological abnormality B" may be displayed in association with the notification information 122. In any case, the playback processing unit 50 displays the notification information 120 and the notification information 122 such that the image interpreter can easily recognize which pathological abnormality is suspected.

Displaying the notification information 120 and the notification information 122 on the timeline 110 allows the doctor B to immediately confirm an endoscopic image that is likely to include a pathological abnormality by placing the mouse pointer on the parts of the timeline 110 in which the notification information 120 and the notification information 122 are displayed. Further, by displaying the notification information 120 and the notification information 122 on the timeline 110, the doctor B can also predict at which site an image with a suspected pathological abnormality has been captured. Although not shown, the playback processing unit 50 may display the time range of an image determined as a bleeding image on the timeline 110.

According to the endoscopic image observation support system 1 of the embodiment, when performing a compression process on an endoscopic RAW image, image analysis on an endoscopic image is performed, and a compressed image is generated in a condition in which the analysis result is added to the compressed image. When the doctor B interprets an endoscopic image, analysis of the endoscopic image has already been completed, and the image processing unit 32 thus does not perform the image process while the endoscopic image is being played back. Therefore, the playback processing unit 50 can promptly display the notification information 120 and the notification information 122 on a selection screen for an endoscopic image, and the image interpretation task performed by the doctor B can be streamlined.

Figure 4:
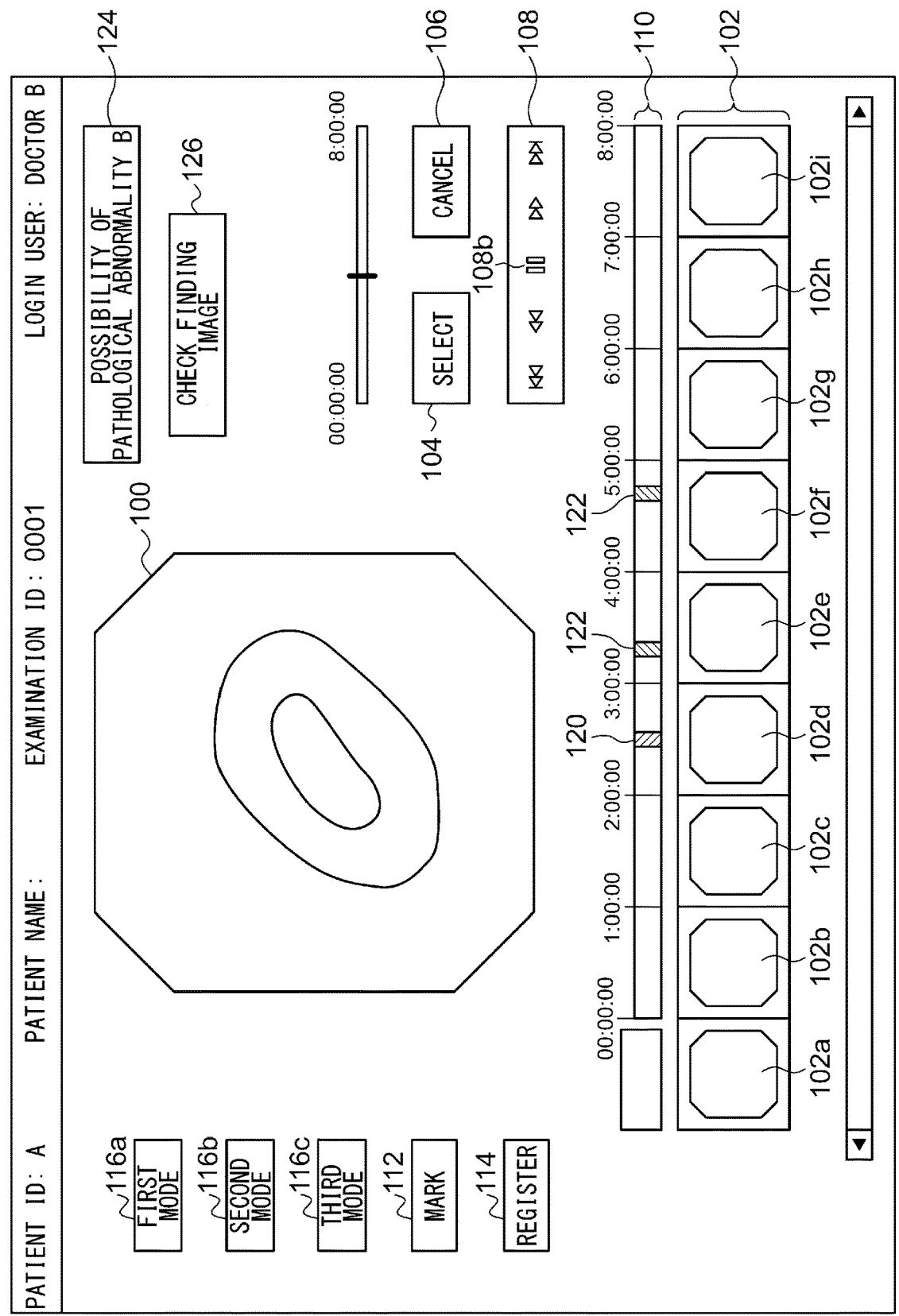
FIG. 4 shows an example of a selection screen occurring while endoscopic images are sequentially displayed.

FIG. 4 shows an example of a selection screen occurring while endoscopic images are sequentially displayed. In the playback area 100, the playback processing unit 50 displays an endoscopic image recorded in the endoscopic image recorder 62. In the following, an explanation will be given regarding a case where the first mode selection button 116a is selected and the playback processing unit 50 plays back an endoscopic image at a constant speed at a playback speed set by the image interpreter. During the image observation, the doctor B may operate the marking button 112 to mark the start position of each site on the timeline 110. While marking the start position of each site, the doctor B performs image observation by selecting an endoscopic image in which a pathological abnormality finding has been captured. Marking makes it easy to know where to start looking when reviewing endoscopic images later.

When an image including a pathological abnormality is displayed in the playback area 100, the doctor B operates the pause button 108b so as to stop displaying images in a switching manner. When the pause button 108b is operated, the playback button 108a is displayed instead of the pause button 108b in the playback operation area 108. The doctor B operates the wheel of the mouse to display images that are before and after an image that has been stopped in the playback area 100 and searches for an image in which a pathological abnormality finding has been clearly captured. In the management server 10, when the reception unit 52 receives operation input from the doctor B, the playback processing unit 50 causes the display device 22 to display an endoscopic image according to the operation input that has been received.

When an image in which a pathological abnormality finding has been captured clearly is displayed in the playback area 100, the doctor B operates the selection button 104. When the reception unit 52 receives selection operation in the management server 10, the playback processing unit 50 captures a selected image displayed in the playback area 100 and displays the image in the selected image display area 102. The image displayed in the selected image display area 102 may be selected as an image attached to an image interpretation report later. FIG. 4 shows that selected images 102a-102i are selected in the selected image display area 102.

While endoscopic images are being played back continuously, the doctor B particularly carefully observes images included in the respective display ranges of the notification information 120 and the notification information 122 displayed on the timeline 110. By displaying the notification information 120 and the notification information 122 on the timeline 110, the risk of overlooking by the image interpreter can be reduced.

When displaying an endoscopic image to which information on a finding is added in the playback area 100, the playback processing unit 50 may display the information on the finding as notification information 124. In this case, notification information 124 indicating "possibility of pathological abnormality B" is displayed. The playback processing unit 50 may display the notification information 124 in such a manner as to attract the attention of the doctor B. For example, the playback processing unit 50 may highlight the notification information 124 by blinking the notification information 124 or may output an alert sound. The outputting of the notification information 124 by the playback processing unit 50 in this manner allows the doctor B to observe an endoscopic image displayed in the playback area 100 with more caution.

The playback processing unit 50 may have a function of displaying a finding image determined to be similar to an endoscopic image. When displaying an endoscopic image to which information on a finding is added in the playback area 100, the playback processing unit 50 operably displays a finding image check button 126 for displaying a finding image determined to be similar to the endoscopic image. When the doctor B operates the finding image check button 126, a finding image determined to be similar to the endoscopic image displayed in the playback area 100 is displayed.

When the notification information 124 indicating "possibility of pathological abnormality B" is displayed for an endoscopic image displayed in the playback area 100, there is a case where the pathological abnormality B cannot be found as a result of image diagnosis by the doctor B. In that case, it is also possible that the finding image determined to be similar is not appropriate, and the doctor B may want to check the finding image in order to improve the accuracy of a future similarity determination. Thus, when the doctor B operates the finding image check button 126, the reception unit 52 receives the button operation in the management server 10, and the playback processing unit 50 displays the finding image determined to be similar in a superposing manner with reference to the finding image ID added to a displayed image. At this time, if the doctor B determines that the finding image is not appropriate as a finding image, the doctor B can perform a registration cancellation operation. When the reception unit 52 receives the registration cancellation operation, the image registration unit 48 deletes the finding image from the finding image recorder 60. The feedback of the result of the image diagnosis given by the doctor B as described allows for the improvement in the similarity determination accuracy.

Next, an explanation will be given regarding a case where the second mode selection button 116b is selected and the playback processing unit 50 plays back, in a switching manner, a group of endoscopic images that has been grouped at a speed higher than that for other endoscopic images. At a speed higher than the playback speed that has been set, the playback processing unit 50 continuously plays back images, from the first image to which the information indicating the start position of the group is added to the last image to which the information indicating the end position of the group is added, in a switching manner. In the second mode, by playing back images included in a group of images with little change at a high speed, the shortening of the overall playback time can be realized.

At this time, if an endoscopic image to which information on a finding is added is present in the group of endoscopic images, the playback processing unit 50 may change the playback speed of the endoscopic image back to normal. This allows the doctor B to carefully observe the endoscopic image to which the information on the finding is added. The playback processing unit 50 may change the playback speed of the endoscopic image to which the information on a finding is added to be slower than normal.

Next, an explanation will be given regarding a case where the third mode selection button 116c is selected and the playback processing unit 50 extracts one or more images from a group of endoscopic images that has been grouped so as to play back the image(s). The playback processing unit 50 plays back one or more images included between an image to which information indicating the start position of the group is added and an image to which the information indicating the end position of the group is added. Regarding the number of images to be played back, for example, several images may be played back. In the third mode, by playing back only several images included in a group of images with little change, the shortening of the overall playback time can be realized.

At this time, if an endoscopic image to which information on a finding is added is present in the group of endoscopic images, the playback processing unit 50 always displays the endoscopic image. Therefore, for example, if the group of endoscopic images is composed of thirty images and there are five endoscopic images to which information on a finding is added, at least the five images are displayed. This allows the doctor B to surely observe the endoscopic images to which the information on a finding is added.

The doctor B operates the registration button 114 when the image observation is ended. When the registration button 114 is operated, a selected image selected in the selected image display area 102 and time information indicating the start position of each site marked by the operation on the marking button 112 are recorded in the observation detail recorder 66 by the management server 10. Thus, the image observation by the doctor B ends.

Described above is an explanation based on the embodiment of the present invention. This embodiment is intended to be illustrative only, and it will be obvious to those skilled in the art that various modifications to constituting elements and processes could be developed and that such modifications are also within the scope of the present invention.

In the embodiment, an image process including a compression process is performed by the management server 10. These image processes may be performed by the capsule endoscope 3 or may be performed by the receiver 4.

What is claimed is:

1. An endoscopic image observation support system comprising:
a processor comprising hardware provided externally of a capsule endoscope, wherein the processor is configured to:
receive, from the capsule endoscope, a plurality of endoscopic images captured by the capsule endoscope; and
perform a compression process on an endoscopic image of the plurality of endoscopic images received from the capsule endoscope,
wherein the processor is configured to, when performing the compression process:
access a finding image recorder that records as a finding image an endoscopic image captured in the past and determined to include a predetermined finding through image diagnosis by a user in the past;
determine whether or not the endoscopic image of the plurality of endoscopic images received from the capsule endoscope is similar to the finding image recorded in the finding image recorder;
in response to determining that the endoscopic image is similar to the finding image, add predetermined information to a compressed image of the endoscopic image generated by the compression process; and
record the compressed image having the predetermined information added thereto in an endoscopic image recorder.

2. The endoscopic image observation support system according to claim 1,
wherein the endoscopic image on which the compression process is performed is a RAW image.

3. The endoscopic image observation support system according to claim 1,
wherein the endoscopic image recorded in the finding image recorder as the finding image is a region of interest in a portion of a larger endoscopic image captured in the past, and
wherein the processor is configured to determine whether or not the endoscopic image of the plurality of endoscopic images received from the capsule endoscope is similar to the finding image by determining whether the endoscopic image of the plurality of endoscopic images received from the capsule endoscope includes a region similar to the region of interest in the finding image.

4. The endoscopic image observation support system according to claim 1,
wherein the processor is configured to control a display to display the compressed image and notification information that is based on the predetermined information added to the compressed image.

5. The endoscopic image observation support system according to claim 4,
wherein the processor is configured to control the display to display information on the predetermined finding as the notification information.

6. The endoscopic image observation support system according to claim 4,
wherein the processor is configured to control the display to display the finding image determined to be similar to the endoscopic image of the plurality of endoscopic images received from the capsule endoscope.

7. The endoscopic image observation support system according to claim 1,
wherein the processor is configured to record the endoscopic image of the plurality of endoscopic images captured by the capsule endoscope and determined to have the predetermined finding as another finding image in the finding image recorder.

8. The endoscopic image observation support system according to claim 7,
wherein the processor is configured to delete the finding image from the finding image recorder based on a user operation.

* * * * *